United States Patent [19]

Outcalt et al.

[11] 4,154,929

[45] May 15, 1979

[54] 9-(2-PYRIDYL)-ACENAPHTHO[1,2-e]-as-TRIAZINES

[75] Inventors: Mark C. Outcalt, Indianapolis; Jerry W. Denney, Carmel, both of Ind.

[73] Assignee: American Monitor Corporation, Indianapolis, Ind.

[21] Appl. No.: 714,481

[22] Filed: Aug. 16, 1976

[51] Int. Cl.$^2$ .................................... C07D 253/08
[52] U.S. Cl. ................................. 544/183; 546/332
[58] Field of Search .................. 260/248 AS; 544/183

[56] References Cited

U.S. PATENT DOCUMENTS

| 4,008,232 | 2/1977 | Lacefield | 260/248 AS |
| 4,033,752 | 7/1977 | Hashimoto et al. | 260/248 AS |

Primary Examiner—John M. Ford
Attorney, Agent, or Firm—Robert A. Spray

[57] ABSTRACT

The discovery of 9-(2-pyridyl)-acenaphtho[1,2-e]-as-triazine and its sulfonated form, having particular advantages when used as both a chelator and indicator of ferrous ions in organic or aqueous mediums; a process for the synthesis of those compounds in which hydrazine is used as both a reactant and as a solvent in production of intermediate compounds, eliminating the need of ethanol and the disadvantageous ether-extraction step; the use of N,N-dimethylformamide as a reaction solvent in the production of triazines; the use of the new triazine compounds to measure iron, transferrin, and UIBC/TIBC in biological systems; the use of dimethylsulfoxide and certain processes to eliminate interferences commonly encountered in these assays; and the use of the triazine compounds to measure both total and/or reduced iron in a variety of matrices.

4 Claims, No Drawings

9-(2-PYRIDYL)-ACENAPHTHO[1,2-e]-as-TRIAZINES

I. INTRODUCTION

The present invention relates to the synthesis of a new and improved compound which is useful for the assay of iron in biological or other aqueous systems, even trace amounts therein, and related concepts detailed herein.

Concepts of the present invention relating to the synthesis of the compound eliminate the need for disadvantageous ether extractions in the production of intermediate products, and provide high yields of a heretofore unknown iron chelator through the use of a new solvent sysem. The use of the new iron chelator increases the sensitivity of prior art assays for iron and for unsaturated iron binding capacity, and reduces interferences from extraneous chromogens and turbidity.

In addition to measuring natively occuring serum iron, the measurement of total iron (after saturation with excess exogenous iron) is used as an indirect measurement of the quantity of transferrin, an iron binding protein present in serum in varying amounts.

These and other specific and overall advantages, which are provided by the present inventive concepts, are set forth and explained in the following description.

II. VITAL SIGNIFICANCE OF ACCURATE IRON ASSAYS

A particular and vitally significant use of iron assays, that is, the determination of the amount of iron ion present, is in the medical field, particularly that of clinical assays of biological fluids.

For example, accurate and reliable iron assays are considered to be very desirable in view of often-vital diagnostic factors such as the following:

In general, increased level of serum iron are associated with:

(a) acute blood loss or increased destruction of red blood cells succh as in hemorrhage, or decreases red blood cell servival;
(b) acute hepatic conditions as in acute hepatitis; cells such
(c) certain sideroachrestic anemias in which there is a decreased utilization of iron stores to produce functional erythrocytes;
(d) ingestion of abnormal amounts of dietary iron; and
(e) certain defects in the storage of iron, such as pernicious anemia.

Decreased plasma iron levels may be associated with:
(a) dietary deficiencies in iron;
(b) chronic blood loss pathologies; or
(c) increased demand on the body stores such as occurs during a normal pregnancy.

Increased levels of circulating transferrin are usually associated with increased production of the globulin representing a physiological response to various states of chronic iron deficiency.[1]Decreased levels of iron binding globulin are usually the result of decreased production as may occur in cirrhosis or may be due to a protein-losing nephritis.

These are merely representative of the vital needs of the physician for accurate and precise quantitation of serum iron and iron binding capacity in biological fluids, to prevent him with a valuable clinical adjunct in the diagnosis and therapeutic management of various disease states. Proper quantitation of these parameters enhances the quality of medical treatment and decreases the chance of potentially life-threatening conditions with their resultant patient suffering and increased medical costs.

Mistaken evaluations of a patient's iron assay can result in mistaken diagnosis, and in correspondingly erroneous specification of subsequent treatment, which at best means at least a costly waste of therapy, and even worse, can lead to a wrong treatment which worsens the patients actual condition; and improper treatment if it occurs may obscure subsequent proper diagnosis and thereby prolong improper treatment. Thus, inaccurate iron assays lead to waste, both, inconvenience, and potential great danger to human life and well-being.

The normal level of circulating iron in plasma or serum is a relatively small or trace amount, that is, in the order of only about 70–165 micrograms per deciliter; and thus any assay system must provide as much sensitivity of the indicator compound as possible in order to effect accurate and precise measurements of this trace element. The present invention includes the devising of a synthesis and utilization of a compound which provides great sensitivity for iron ion in addition to other advantages.

Another practical advantage of this assay of iron and its associated transport globulin is that the method is rapid easily performed, and free from potential sources of interference or error.

III. DISADVANTAGES OF PRIOR ART

Prior art synthesis of the general class of triazine type compounds in general included the use of an alcoholic solvent. This necessitated a tedious as well as dangerous ether extraction step; for the intermediate reaction product, 2-pyridylhydrazidine, is soluble in low carbon aliphatic alcohols. The present invention permits and achieves the total avoidance of alcohol as a solvent, and permits and achieves the total avoidance of alcohol as a solvent, and permits and achieves the total avoidance of the ether extraction procedure.

Prior art metods for the assay of iron in biological fluids, in general, fall short in one or more of the characteristics of the present invention.

As iron is usually encountered in plasma complexed with an iron binding protein (i.e., transferrin), a first accomplishment of the present invention is the rapid removal of iron from the protein, thus enabling it to bind to the new iron chelator used for detection.

Early prior art methodologies affected the disruption of the complex by the utilization of highly acidic conditions with concommitant precipitation of proteins present in the sample. This appraoch, however, in addition to being cumbersome, time-consuming, and laborious, has disadvantages in terms of quality of result, such as:

(1) The conditions employed are not effective in removal of all of the iron from the protein; thus some of the iron is co-precipitated with the protein. [2] This yields results which are too low, indicating an iron-deficiency when perhaps none exists, and other erroneous diagnoses.

(2) Precipitation of the protein causes a decrease in the volume of the assay leading to an overestimation of the iron present in the original sample by as much as 5–10%, depending on the concentraton of protein present. This may give such a high reading as to mask an acutal iron-deficient state.

(3) Very often the conditions employed were not sufficient to remove all of the protein present, yielding a slightly turbid supernatant solution which led to further error in the analysis. This turbidity leads to a likely overly high reading due to the light-scattering properties of the turbid material, resulting again in a possible overestimation of iron content and attendant mis-diagnosis of clinical mismanagement.

(4) The additional procedural steps involved in this precipitation cause greater exposure to or possibility of contamination with exogenous iron in glassware or other laboratory apparatus, particularly considering the trace quantities which are being measured by the procedure.

(5) Lipemia (a collodial suspension of fat miscelles), when present in serum, is not completely removed. This results in turbidity and interference in the subsequent assay for iron.

(6) Because the majority of iron in the body is contained in hemoglobin, contamination of the specimen with hemoglobin from red blood cells (hemolysis) may cause this iron to be mistakenly measured as serum iron due to the release of iron from hemoglobin under prolonged exposure to strongly acid conditions in the protein precipitation step. [3]

Later approaches have attempted to use less drastic means of liberating iron from transferrin and to dialyze the liberated iron into a recipient fluid where it might be quantitiated in the absence of interfering protein. Although representing certain advantages over methodologies which require precipitation of proteins, this methodology suffers drawbacks concerned with the effects of Donnan equilibrium, [4] which concerns itself with the effects of non-iron constituents on the rate of dialysis of iron ions. In the dialysis methodologies, the introduction of a lipemic sample may seriously alter the characteristics of the membrane used for dialysis, producing problems not only in the affected specimen but also in other specimens which may be analyzed subsequent to the introduction of the lipemic sample.

In addition, this methodology requires expensive ancillary equipment, which frequently necessitates considerable maintenance.

More recently, direct serum approaches have utilized the mass action principle to liberate iron from transferrin. More specifically, the use of mild acid conditions and a high ratio of soluble chromogen to iron, while eliminating some but not all the disadvantages of prior art methodologies heretofore discussed, have introduced new interferences or have caused interfering substances present in earlier prior art merely to change their mechanism of interference. Endogenous serum chromogens such as bilirubin or carentoids, wich represented only minor interferences in the protein precipitaton or dialysis techniques, are much more significant causes of interference, and consequent error.

Hemoglobin, which in the protein precipitation methodologies produced interference due to liberation of iron from the hemoglobin molecule, may cause spurious results in the direct serum procedures due to native color of hemoglobin and its contribution to the total color measured in the procedure, that color being falsely assumed to be due to the presence of iron in serum. However, while the interference of hemoglobin in these procedures is to a degree explained by the above rationale, results obtained by the use of the serum blanks in some prior art techniques suggest the hemoglobin may cause extensive interference even beyond that introduced by its native color.

Lipemia, which interfered with earlier prior art methods, also may interfere with direct serum methods, because the turbidity of the sample still remains in the test at the time the color measurement is made. (Color measurements are made by determining the amount of light absorbed by the chromophore produced by the reaction of iron with a chromogen.) The turbidity has the effect of absorbing light, and may be interpreted as chromophore and thus as iron. Serum blank corrections have been attempted by prior art methods to correct for turbidity. However, the amount of light absorbed due to turbidity is often great relative to the amount of light absorbed by the chromophore. Thus a slight error in the turbidity correction may produce a large effect on the chromophore measurement, thereby producing an error in the quantitation of iron in the lipemic sample.

Atomic absorption methodologies measure the iron by utilization of highly characteristic atomic resonance bands. However, since all iron present in the sample exhibits such bands, hemoglobin (which contains iron) causes positive interference and corresponding error.[5] Further, because of the limited sensitivity of atomic absorption spectrophotometers and the relatively low iron concentration present in biological fluids, large sample dilutions (which commonly are employed to minimize the effects of protein-induced viscosity on flow rates) are prohibited.[6] Thus, varying protein concentrations in the original specimen (which occur from one patient to another) may lead to erroneous test results due to the effects of differing viscosities on the flow rate.

IV THE PRESENT INVENTION SUMMARIZED

The present invention overcomes disadvantages of prior iron chelators and the methodologies in which they are employed.

More particularly, the present inventive concepts comprise an improved general synthesis for the general class of compounds known as triazines, whereby the tedious and dangerous ether extraction step is avoided and whereby greater percentage yields are obtained through the use of N,N-dimethylformamide as a solvent in the synthetic process; the synthesis of new iron chelators, 9-(2-pyridyl)-acenaphtho [1,2-e]-as-triazine and its sulfonated analog; the use of the sulfonated chelator to measure iron in aqueous systems in such a way that the effects of certain interfering substances are minimized or avoided; the use of dimethylsulfoxide to accelerate the removal of iron from its transferrin complex, thereby speeding the overall assay for iron in serum, and to diminish turbidity due to lipemia and/or protein; the discovery of a process or method which minimizes certain interferences of hemoglobin in the assay; and the means of standardization and calculation of results which eliminate error of prior art means whenever the reagents are mildly contaminated with exogenous iron.

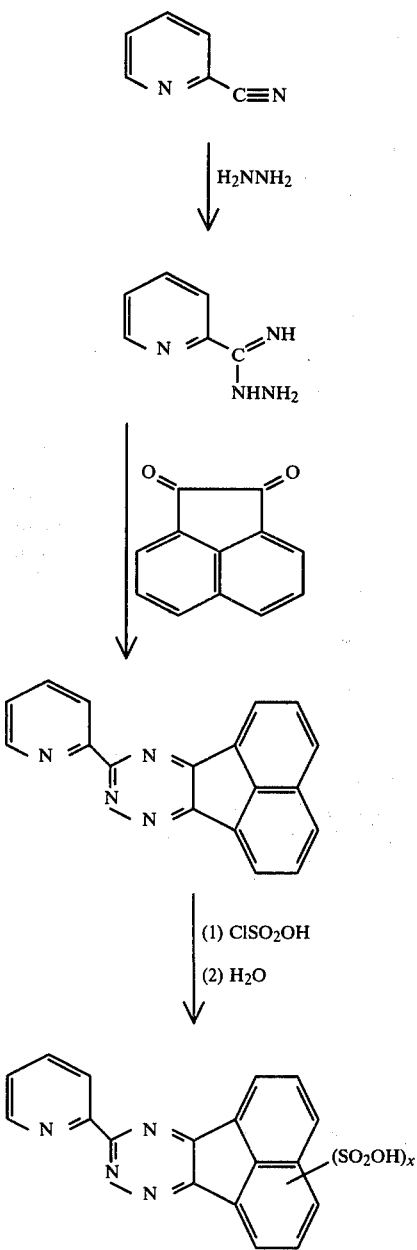

V. SYNTHESIS AND ADVANTAGES OF 9-(2-pyridyl)-acenaphtho [1,2-e]-as-triazine AS AN IRON CHELATOR As shown in the drawing, and in carrying out the invention in a preferred form, the following sets forth the inventive concepts relating to the synthesis of a sulfonated triazine compound stepwise as follows:

(1) Preparation of 2-pyridylhydrazidine

2-Pyridiylhydrazidine was prepared by a modification of the method previously reported by Case.[7] Case employed ethanol as a solvent; however, in this present synthesis, the inventive concepts here provide that hydrazine (a highly poisonous and explosive agent and which is structurally quite unrelated to the solvents heretofore used) is used as the solvent. The hydrazine, which is present in stoichiometric excess, was found to provide the double function of serving both as a reactant and a solvent.

In the absence of ethanol, which the Case prior art used as a solvent, but which here is avoided, the hydrazidine crystallizes out of solution when the reaction mixture is poured into water; this obviates the bothersome, extra and dangerous ether extraction procedure which is necessary when ethanol is used, that extraction being then required due to the high solubility of the product in an ethanol and water mixture. The use of hydrazine as a solvent also permits the use of higher reaction temperatures. Use of hydrazine in this manner results in a percentage yield which is greater than has been reported in the Case citation.

In the present synthesis, a 728.77 gram (7 mole) quantity of 2-cyanopyridine was slowly poured with stirring into 1,000 milliliters of 95+% hydrazine. When the mildly exothermic reaction was over, as indicated by a drop in the temperature of the reaction mixture, the reactants were heated in a water bath for 5 hours at 99±1° C. The reaction mixture was allowed to cool to room temperature, poured with stirring into 1500 milliliters of cold water, and allowed to remain overnight (approximately 18 hours) at 4° C. The crystals formed in this process were then vacuum filtered, washed with ice water, and vacuum dried at room temperature. The dried material weighed 804.0 grams (84% yield) with a melting point of 95° C.

(2) Preparation of 9-(2-pyridyl)-acenaphtho [1,2-e]-as-triazine

This new triazine compound, which subsequently was shown to possess extremely desirable characteristics when used as an iron chelator in assays for iron, was prepared by reacting the 2-pyridylhydrazidine with acenaphthoquinone. (The procedural steps as detailed below are essentially modifications of those used by the Case method[8] to prepare various other triazine products which do not provide the advantages of the triazine of the present invention.)

Additionally, N,N-dimethylformamide (a material structurally quite unrelated to and less dangerous than ethanol) was provided as a solvent instead of ethanol as in the Case method, providing greater yields of the desired condensation produce than occurs when ethanol is similarly used. (This seems to be most likely due to the low solubilities of the reactant, acenaphthaquinone, and the product of the reaction, 9-(2-pyridyl)-acenaphtho[1,2-e]-astriazine, in ethanol).

More specifically, to a slurry of 1,093 grams (6 moles) of acenaphthenequinone in 6 liters of N,N-dimethylformamide, 820 gram (6 moles) of 2-pyridylhydrazidine was added in small portions with constant mixing. (Most of the suspended solids had dissolved by completion of the additions.) When the initial slightly exothermic reaction was complete, the reaction mixture was maintained at 105°-110° C. for 24 hours by heating.

The reaction mixture was then cooled to 45° C. and poured with stirring into 16 liters of ice water. The solid which was formed was vacuum filtered and pressed dry as possible. This material, which holds water tenaciously, was allowed to air dry for several weeks, then ground to a fine powder. This was slurried with 4 liters of boiling benzene and filtered after cooling to room temperature. This last step was repeated three more times and the resultant solid vacuum dried.

The resultant material had a melting point of 198°-200° C. (uncorrected), was greenish yellow in appearance, and weighed 1,093 grams, representing a 65% theoretical yield. A small portion of the material was twice recrystalized from benzene to give a material with a melting point of 201° C. (decomposition) and an elemental analysis in agreement with 9-(2-pyridyl)-acenaphtho [1,2-e]-as-triazine (Molecular Formula $C_{18}H_{10}N_4$).

Elemental analysis calculated weight percentages for $C_{18}H_{10}N_4$ is as follows:

|  | Calculated | Found |
| --- | --- | --- |
| Percent C | 76.58 | 76.18 |
| Percent H | 3.57 | 3.74 |
| Percent N | 19.85 | 20.10 |

(3) Sulfonation of 9-(2-pyridyl)-acenaphtho [1,2-e]-as-triazine

The following procedure was carried out to effect solubilization in an aqueous system of the triazine prepared in the above synthesis.

A 1000 gram (2.54 moles) quantity of 9-(2-pyridyl)-acenaphtho[1,2-e]-as-triazine was added in small portions with stirring, to 3000 grams (1.7 liters) of chlorosulfonic acid (iron free). During the exothermic reaction, the mixture was maintained at 5°-10° C. by immersion in an ice bath. The mixture was then allowed to stand at room temperature overnight (approximately 18 hours), and then heated to 150° C. for 96 hours. The mixture was then cooled to 5° C., and the viscous liquid carefully poured onto 4000 grams of crushed ice prepared from deionized water. (Extreme caution should be exercised in this last step due to the very vigorous reaction between chlorosulfonic acid and water and the evolution of hydrogen chloride gas.)

The solid which formed was vacuum filtered on a sintered glass funnel and then suspended in 3 liters of water and heated to boiling for 30 minutes. The solid was again filtered and washed four times with 500 milliliter portions of water. The damp solid was then dissolved in a minimal amount of concentrated ammonium hydroxide, and the dark brown solution was filtered to remove any undissolved material. The solution was acidified with concentrated hydrochloric acid until no more solid formed upon further addition of acid. The solid was filtered, resuspended in two liters of warm water, and again filtered.

This washing was repeated three more times; each time the material was pressed as dry as possible. After the last water wash, the material was suspended in two liters of methanol and heated to boiling, cooled to room temperature and filtered. The resulting solid was vacuum dried at room temperature, ground to a fine powder and vacuum dried at 110° C., resulting in 629 grams of solid material, having the desired water soluble properties.

This material is probably a mixture of various isomers of sulfonic acids of the initial triazine. A satisfactory analysis for a single compound containing eighteen carbon and four nitrogen atoms could not be obtained. The somewhat hygroscopic material melted at 350° C. with decomposition and had a molecular weight of 560 as determined by spectrophotometric titration with ferrous iron, based on a complex of three ligand molecules per iron atom.

(4) Advantages of the 9-(2-pyridyl)-acenaphtho [1,2-e]-as-triazine as chelator The new triazine compound prepared by the above procedure was shown to have extremely desirable characteristics when used as a chelator in the quantitative estimation of ferrous iron in aqueous systems.

In examining these characteristics, it was found that the maximum spectral absorbance of the iron-chromogen complex occurs at 610 nm. Absorbance measurements of this wavelength provide a distinct advantage in that it is far removed from the absorption peaks of interferences commonly encountered in serums, and, secondly, aids in the minimization of false positive absorbances due to the effects of turbidity and lipemia.

In comparision with, and in contrast to, prior art chelators, this new compound of the present invention demonstrated extremely good sensitivity characteristics.

While some prior art compounds were possessed of good sensitivity for iron and others showed absorbances in a preferred portion of the spectrum, no single prior art compound possessed both characteristics in combination.

Additonally, as the sulfonated form of the triazine shows good solubility in aqueous systems, the use of this form in an aqueous system avoids some of the problems attendant in prior art methods which required protein precipitation due to the incompatability of the proteins present in the sample with the chemicals used to solvate the chelator.

VI. ASSAY SYSTEM FOR THE QUANTITATION OF SERUM IRON

(a) First Embodiment

STEP I:

In carrying out the invention in a desired embodiment for the quantitation of serum iron, the inventive concepts herein provide for the addition of the sample to an acidic buffer containing dimethylsulfoxide and surfactants. While this step not only provides for the liberation of transferrin bound iron, use of the dimethylsulfoxide and surfactants provides for increased protein solubilization, an increased rate of iron liberation, and helps minimize the effects of turbidity and/or lipemia which may be present in the serum.

In a specific desired form, the quantities and other particulars are:

0.5 ml of serum or standard is added to 2 cc of a 0.5 molar acetate buffer, pH 4.5, containing 10% (V/V) dimethylsulfoxide, 5 ml/L Brij 35, 3ml/L Triton X-100, and 0.384 g/L of magnesium acetate, resulting in a dimethylsulfoxide concentration of approximately 7.0% (V/V) in the final reaction mixture. The reductant consists of 0.1 ml of a 25% (W/V) solution of ascorbic acid.

After allowing the mixture to stand for five minutes, the absorbance is read at 610 nm.

If the sample contains hemoglobin, it has been found that the inclusion of a five minute incubation prior to the first absorbance measurement virtually eliminates the interferences due to hemoglobin, both those contributed by its native color as well as those caused by other factors, as contrasting with prior art serum blanking procedures which failed to recognize the critical timing involved.

STEP II:

In a second step (after the absorbance of the above mixture has been recorded) a solution of chromogen is added and allowed to complex the ferrous ions present in solution, the chromogen according to the inventive concepts being an aqueous solution of the 9-(2-pyridyl)-acenaphtho[1,2-e]-as-triazine sulfonate as mentioned above, the solution being prepared by adding the proper amcunt of the chelator to water, and adjusting pH with dilute sodium hydroxide until solution occurs, usually when a pH of 4.5 is reached. In a specific desired embodiment, 0.1 milliliters of a 0.01M solution (0.02%, W/V, in the final reaction mixture of the 9-(2-pyridyl)-acenaphtho[1,2-e]-as-triazine sulfonated is added to the solution from Step I above, and allowed to react for approximately five minutes; and the final absorbance read at a wavelength of 610 nanometers.

STEP III

The total iron present in the original sample is calculated by subtracting the absorbance measurement obtained in Step I above from that obtained in Step II, this difference representing the quantitation of iron-chelator complex present in the solution. This absorbance difference is then compared to the absorbance response of a solution of known iron content, which has been subjected to the same treatment, for the purpose of translating absorbance response to an iron concentration term.

(b) Other alternative embodiments

The operating concepts set forth in what is described above as a desired first embodiment for the assay of serum iron may be advantageously utlized in other embodiments of an assay for iron in aqueous systems.

For example, in Step I above the specimen containing iron is reacted with an acetate buffer containing dimethylsulfoxide, pH 4.5, to liberate bound iron. While the inclusion of dimethylsulfoxide represents high advantages for some specimens, it is not essential to proper performance on most specimens, and its deletion should not affect performance of the assay depending upon the matrix in which the iron was located. Acidic conditions are employed in a first step of the procedure in order to facilitate removal of iron from transferrin. In the first desired embodiment described above, an acetate buffer, pH 4.5, was utilized to this end. Alternatively, other buffers such as malate, succinate, and glycine may be used without departing from the inventive concepts herein described.

While Brij-35 and Triton X-100 are the surfactants in a first desired embodiment as described above, other surface active agents may be used.

VII. ASSAY SYSTEM FOR THE QUANTITATION OF UNSATURATED IRON BINDING CAPACITY

(a) First Embodiment

STEP I

A first step in carrying out the concepts of the present invention, as applied to the assay of unsaturated iron binding capacity in serum, is to combine serum containing transferrin with a buffered alkaline solution of excess ferrous iron, i.e., excess ferrous ion relative to the absolute binding capacity of the serum sample. A reductant is added to this combination. After allowing sufficient time for the saturation of transferrin with ferrous ion to occur, an initial optical density of the solution is recorded at 610 nm. This absorbance measurement is subtracted from a final absorbance reading, and serves the purpose of correcting for erroneous absorbance measurements due to varying absorbance of the serum itself.

In a specific desired form, the quantities and other particulrs are:

a. 0.5 milliliters of serum containing a quantity of transferrin is combined with 2.0 milliliters of a buffered ferrous reagent containing 150 mg/L of iron and an amount of citric acid which is equimolar to the amount of iron added in a Tris buffer, pH 8.4, and mixed.

b. To this mixture 0.1 ml of a 25% (W/V) solution in water of ascorbic acid is added, the mixture is allowed to stand for at least 5 minutes, and the absorbance is recorded at 610 nm.

STEP II

To the extent that unbound transferrin saturates itself, the measurable iron (i.e., non-transferrin bound iron) content of the added solution will be depleted. Thus in a second step only this non-transferrin bound iron remaining in the mixture is quantitated by the addition of a solution containing the newly synthesized iron chelator, allowing the chelation process to go to completion by incubating for 5 minutes at room temperature. The measurable iron content of the mixture is then calculated by determining the resultant absorbance at a wavelength of 610 nm.

In a specific desired form, the quantities and other particulars are:

0.1 milliliters of a 0.01 M solution of 9-(2-pyridyl)-acenaphtho[1,2-e]-as triazine sulfonate, pH 4.8, is added to the mixture from Step I above, resulting in a concentration of 0.02% W/V in the final reaction mixture, and allowed to react for approximately 5 minutes at room temperature. The developed chromophore is then measured at 610 nm and the absorbance recorded.

STEP III

Serum unsaturated iron binding capacity is then calculated by subtracting the absorbance of Step I from the absorbance obtained in Step II, and comparing this with the absorbances of solutions containing a known amount of iron. The resultant figure is then an expression of the amount of iron which remained in solution and was not bound by transferrin.

The amount of iron added initially by the reagents in the assay is measured by subjecting a sample of iron-free water to the same procedural steps as are followed for an unknown in Steps I and II above, said measurement hereinafter referred to as the "water reference" measurement.

Subtraction of the amount of non-transferrin bound iron, from the amount added (as determined by the "water reference"), gives a direct measure of unsaturated transferrin, stated as unsaturated iron binding capacity, in terms of the iron taken up.

More specifically, unsaturated iron binding capacity is calculated by use of the following formula:

$$A_{H_2O} - [A_2 - A_1] = \text{Absorbance Equivalent of bound iron}$$

in which $A_{H_2O}$ represents the absorbance of the water reference, $A_2$ represents the absorbance of the unknown as determined in Step II above, and $A_1$ represents the absorbance of the unknown obtained in Step 1.

Use of this mathematical procedure by the analyst automatically corrects for the possibility of trace contamination of the reagents with iron. By measuring a water reference in each assay, and its use in the above calculation, added iron, as well as trace contamination which has the effect of additional iron, is measured and accounted for, eliminating the need for re-standardization each time the procedure is used.

VIII. SUMMARY OF ACHIEVEMENTS AND ADVANTAGES OF INVENTIVE CONCEPTS

The concepts of the present invention thus provide the following achievements and advantages:

(a) A new triazine compound, 9-(2-pyridyl)-acenaphtho[1,2-e]-as-triazine, and the sulfonated form thereof;

(b) The use of those triazine compounds as both a chelator and indicator of ferrous ions, providing advantages of exhibiting a combination of good sensitivity and maximum spectral absorbance in a region far removed from the effects of commonly encountered interferences, thus improving reliability of the assay;

(c) The use of hydrazine as both a reactant and a solvent in the preparation of hydrazadine intermediate compounds, thus obviating the need for ethanol and the need for ether extractions and achieving the avoidance of the disadvantages inherent in such extra extraction steps.

(d) The use of N,N-dimethylformamide as a solvent in the production of triazine compounds, providing for greater yields of the desired triazine;

(e) The use of dimethylsulfoxide in an aqueous system for the quantitative estimation of iron or unsaturated iron binding capacity, effecting an increased rate of iron liberation, minimization of the effects of turbidity and/or lipemia, and providing for increased protein solubilization;

(f) The procedural step in the determination of iron in biological systems in which the incubation time is extended, aiding in reducing interferences encountered when hemolyzed specimens are used;

(g) A novel procedural process for the determination of unsaturated iron binding capacity, which eliminates errors caused by contamination of the reagent system with exogenous iron; and (h) The use of the new triazine compound, and its sulfonated form, to provide for a determination of the total and/or reduced iron present in a variety of matrices.

IX. CONCLUSION

Accordingly, it will thus be seen from the foregoing description of the invention according to the embodiments of the invention herein set forth, that the present invention provides a new and useful compound and assay primarily for serum iron (ferrous) determination, and provides a novel and advantageous method and reagents therefor, all having desired advantages and characteristics, and accomplishing the objects of the invention including the objects herein before pointed out and others which are inherent in the invention.

It will be understood that certain modifications and variations of the specific and general concepts of the invention may be effected without departing from the many concepts heretofore described; accordingly, the invention is not to be considered limited to the specific form or embodiments set forth herein for the purpose of disclosing and illustrating the inventive concepts discovered and herein applied. For example, although the present assay system dwells primarily on the determination of ferrous iron in serum, the principles and concepts set forth would apply advantageously to the determination of iron in other aqueous systems, such as waste water, sea water, and other aqueous chemical solutions.

REFERENCES

1. Searcy, Ronald L.; *Diagnostic Biochemistry*, p. 332 (McGraw Hill, 1969)
2. Henry, R. J., Cannons, D. C. & Winkelman, J.W.; *Clinical Chemistry: Principles and Techniques*, p. 680 (Harper & Row, 2nd Ed., 1974)
3. Ibid., p. 684
4. Babson, A. L. & Kleinman; *Clinical Chemistry*, Vol. 13, No. 2, p. 163 (1967)
5. Henry, op. cit., p. 681
6. Ibid.
7. Case, F. H.; *Journal Organic Chem.*, Vol. 30, p. 931 (1965)
8. Ibid.

What is claimed is:

1. 9-(2-pyridyl)-acenaphtho[1,2-e]-as-triazine.

2. The compound as set forth in claim 1 in its sulfonated form, 9-(2-pyridyl)-acenaphtho[1,2-e]-as-triazine sulfonate.

3. In a process for preparing 1,2,4-triazines by the condensation of hydrazidines and 1,2-diketones, the use of N,N-dimethylformamide as a reaction solvent in the condensation step.

4. In the process as set forth in claim 3, in which the diketone is acenapthoquinone, the use of N,N-dimethylformamide as a reaction solvent in the condensation reaction between 2-pyridylhydrazine and acenaphthoquinone.

* * * * *

UNITED STATES PATENT AND TRADEMARK OFFICE
CERTIFICATE OF CORRECTION

PATENT NO. : 4,154,929         Page 1 of 3
DATED      : May 15, 1979
INVENTOR(S): Mark C. Outcalt et al.

It is certified that error appears in the above—identified patent and that said Letters Patent is hereby corrected as shown below:

In the Title; Abstract, line 1; column 4, line 52; column 5, line 52; column 6, line 31; column 7, lines 6, 19 and 24; column 8, line 3; column 9, lines 6 and 13; column 10, line 32; column 11, line 13 and column 12, lines 38 and 40; Throughout the entirety of the printed patent, the underscoring of the "e" and the "as" in the name of the triazine compound, has been omitted.

Column 1, line 20, "occuring" should read -- occurring --.
Column 1, line 41, "succh" should read -- such --.
Column 1, line 41, "decreases" should read -- decreased --.
Column 1, line 42, "servival" should read -- survival --.
Column 1, lines 43 and 44, delete "cells such".
Column 1, line 66, "prevent" should read -- provide --.
Column 2, line 10, "patients" should read -- patient's --.
Column 2, line 13, "both" should read -- bother --.
Column 2, line 27, after "rapid" insert a comma (,).

UNITED STATES PATENT AND TRADEMARK OFFICE
CERTIFICATE OF CORRECTION

PATENT NO. : 4,154,929

DATED : May 15, 1979

INVENTOR(S) : Mark C. Outcalt et al.

It is certified that error appears in the above—identified patent and that said Letters Patent is hereby corrected as shown below:

Column 2, lines 37 through 39, delete "and permits and achieves the total avoidance of alcohol as a solvent,"

Column 2, line 49, "affected" should read -- effected --.

Column 2, line 52, "appraoch" should read -- approach --.

Column 3, line 6, "of" should read -- or --.

Column 3, line 13, "miscelles" should read -- micelles --.

Column 3, line 52, "wich" should read -- which --.

Columh 4, line 2, "methods," should read -- methods --.

Column 5, line 60, "Pyridiylhydrazidine" should read -- pyridylhydrazidine --.

Column 6, line 49, "astriazine" should read -- as-triazine --.

Column 6, line 49, "ethanol)." should read -- ethanol.) --.

Column 8, line 64, "contrasting" should read -- contrasted --.

Column 9, line 13, "sulfonated" should read -- sulfonate --.

Column 10, line 5, "particulrs" should read -- particulars --.

Column 10, line 32, "as triazine" should read -- as-triazine --.

UNITED STATES PATENT AND TRADEMARK OFFICE
CERTIFICATE OF CORRECTION

PATENT NO. : 4,154,929                Page 3 of 3

DATED      : May 15, 1979

INVENTOR(S) : Mark C. Outcalt et al.

It is certified that error appears in the above—identified patent and that said Letters Patent is hereby corrected as shown below:

Column 10, line 61, "$A_{H2}O-$" should read -- $A_{H_2O}$ --.

Column 10, line 63, "$A_{H2O}$" should read -- $A_{H_2O}$ --.

Signed and Sealed this

Fifteenth Day of July 1980

[SEAL]

Attest:

SIDNEY A. DIAMOND

Attesting Officer    Commissioner of Patents and Trademarks